US008232454B2

(12) United States Patent
Yeh et al.

(10) Patent No.: US 8,232,454 B2
(45) Date of Patent: Jul. 31, 2012

(54) GENE-TRANSFER VECTOR COMPRISING HELPER-COMPONENT PROTEASE GENE OF PAPAYA RINGSPOT VIRUS FOR BROAD-SPECTRUM VIRUS RESISTANCE IN CROPS AND USE THEREOF

(76) Inventors: Shyi-Dong Yeh, Taichung (TW);
Yi-Jung Kung, Taichung (TW);
Hui-Chin Wang, Taichung (TW);
Shin-Lan Wang, Taichung (TW)

( * ) Notice: Subject to any disclaimer, the term of this patent is extended or adjusted under 35 U.S.C. 154(b) by 112 days.

(21) Appl. No.: 12/784,449

(22) Filed: May 20, 2010

(65) Prior Publication Data

US 2011/0289624 A1    Nov. 24, 2011

(51) Int. Cl.
C12N 15/82    (2006.01)
C12N 15/57    (2006.01)
C12N 1/21    (2006.01)
A01H 5/00    (2006.01)
A01H 5/10    (2006.01)

(52) U.S. Cl. .............. 800/279; 435/320.1; 435/419; 435/468; 435/469; 435/252.3; 800/295

(58) Field of Classification Search .............. 800/279, 800/285
See application file for complete search history.

(56) References Cited

U.S. PATENT DOCUMENTS 5,169,770 A * 12/1992 Chee et al. ............... 800/294

OTHER PUBLICATIONS

Yap et al. N-terminal of Papaya ringspot virus type-W (PRSV-W) helper component proteinase (HC-Pro) is essential for PRSV systemic infection in zucchini (2009) Virus Genes 38: 461-467.*
Anandalakshmi et al. A viral suppressoe of gene silencing in plants (1998)) PNAS 95: 13079-13084.*
Kasschau et al. P1/HC-Pro, a viral suppressor of RNA silencing, interferes with Arabidopsis development and miRNA function (2003) Dev. Cell 4: 205-2017.*
Lehner et al. How to use RNA interference (2004) Breif. Func. Genom. Prot. 3: 68-83.*
Xing Ming Shi et al., Mutations in the Region Encoding the Central Domain of Helper Component-Proteinase (HC-Pro) Eliminate Potato Virus X/Potyviral Synergism, Virology, vol. 231, 1997, pp. 35-42.
Paula Tennant et al., Papaya Ringspot Virus Resistance of Transgenic Rainbow and SunUp is Affected by Gene Dosage, Plant Development, and Coat Protein Homology, European Journal of Plant Pathology, 2001, pp. 645-653, vol. 107, Kluwer Academic Publishers, Netherlands.
S.-D. Yeh et al., Comparative Studies on Host Range and Serology of Papaya Ringspot Virus and Watermelon Mosaic Virus 1, Phytopathology, 1984, pp. 1081-1085, vol. 74.
Shyi-Dong Yeh, Doctoral Dissertation: Factors of Papaya Ringspot Virus Affecting Strain-Specific Cross Protection and Transgenic-Resistance Breakdown, Department of Plant Pathology National Chung Hsing University, Jan. 2005.
Savarni Tripathi et al., The Ability of Papaya Ringspot Virus Strains Overcoming the Transgenic Resistance of Papaya Conferred by the Coat Protein Gene is not Correlated with Higher Degrees of Sequence Divergence from the Transgene, European Journal of Plant Pathology, 2004, pp. 871-882, vol. 110, Kluwer Academic Publishers, Netherlands.
C.-H. Wang et al., Divergence and Conservation of the Genomic RNAs of Taiwan and Hawaii Strains of Papaya Ringspot Potyvirus, Archives of Virology, 1997, pp. 271-285, vol. 142, Austria.
Shyi-Dong Yeh et al., Complete Nucleotide Sequence and Genetic Organization of Papaya Ringspot Virus RNA, Journal of General Virology, 1992, pp. 2531-2541, vol. 73, Great Britain.
Anandalakshmi, R. et al., A viral suppressor of gene silencing in plants,Proc. Natl. Acad. Sci. USA,vol. 95, pp. 13079-13084, Oct. 1998.
Huey-Jiunn Bau et al., Broad-Spectrum Resistance to Different Geographic Strains of Papaya ringspot virus in Coat Protein Gene Transgenic Papaya, Phytopathology, 112-120, vol. 93, No. 1, 2003.
Huey-Jiunn Bau et al., Field Evaluation of Transgenic Papaya Lines Carrying the Coat Protein Gene of Papaya ringspot virus in Taiwan, Plant Disease, 2004, 594-599, vol. 88 No. 6.
Gianinna Brigneti et al., Viral pathogenicity determinants are suppressors of transgene silencing in Nicotiana benthamiana, The EMBO Journal, vol. 17 No. 22 pp. 6739-6746, 1998.
Ying-Huey Cheng et al., Efficient transformation of papaya by coat protein gene of papaya ringspot virus mediated by Agrobacterium folloMng liquid-phase wounding of embryogenic tissues with caborundum, Plant Cell Reports,1996, 16:127-132.
Maureen M.M. Fitch et al., Virus Resistant Papaya Plants Derived from Tissues Bombarded with the Coat Protein Gene of Papaya Ringspot Virus, Biotechnology, 1992, vol. 10, pp. 1466-1472.
Yi-Jung Kung et al., Generation of Transgenic Papaya with Double Resistance to Papaya ringspot virus and Papaya leaf-distortion mosaic virus, Phytopathology, 2009, vol. 99, pp. 1312-1320.
Yi-Jung Kung et al., Generation of hermaphrodite transgenic papaya lineswith virus resistance via transformation of somatic embryos derived from adventitious roots of in vitro shoots, Transgenic Res., online DOI: 10.1007/s11248-009-9344-2, 2009.
Sanford, J. C. et al., The Concept of Parasite-Derived Resistance—Deriving Resistance Genes from the Parasites own Genome, J Theor Biol., 1985, vol. 113, pp. 395-405.

* cited by examiner

Primary Examiner — Russell Kallis
Assistant Examiner — Steven Bernacki
(74) Attorney, Agent, or Firm — WPAT, P.C.; Anthony King

(57) ABSTRACT

Provided is a recombinant plasmid having a control sequence and a coding sequence fragment of Papaya ringspot virus (PRSV) helper-component protease gene (HC-Pro gene) operably linked to the control sequence. A recombinant microorganism derived therefrom is also provided. A method for providing plants with resistance against virus is also provided. Use of PRSV HC-Pro gene or fragment thereof in generating plants with resistance against virus is also provided. It is proven that the PRSV HC-Pro transgenic plants can solve the problem resulting from breakdown by gene silencing suppression and provide broad-spectrum resistance to various PRSV strains of different geographical origins.

15 Claims, 8 Drawing Sheets

```
     1210       1220       1230       1240       1250       1260       1270       1280       1290       1300
      |....|....|....|....|....|....|....|....|....|....|....|....|....|....|....|....|....|....|....|....|
519  GCAGAACTGCCGCGGAATTTTAGTGGATCACCGACAGAAGACACGTAATGCACGTAATCGTTTGGATCTGTTGATTCGTTGATTCTGGATATCATATACTGAAGGCTA
YK   .G..T.....................................................................................
HA   ..T.A.....C.............................A......T.C.C.......T....G.C.G.................T.......A.
TH   .G..T......CC.C..T......................A......T.C...........C.G.....................T......G.
MX   ....T......C...........................C.......T.C.......G....G.C.G..................G.........A.

1310       1320       1330       1340       1350       1360       1370
      |....|....|....|....|....|....|....|....|....|....|....|....|....|..
519  ACACAGTTAATCAGTTGATCCAATTCGCTAGAGAAACCGCTCGATAGTGAAATGAAACACTACATTGTCGGT
YK   ......................G......C...........G..........................
HA   ..T...C...C.............G...C..A.......G......................C
TH   ......C........T.G....C......G........A.........................C
MX   ..........C..T.........................A..............T........
```

FIG. 5D

SEQUENCE LISTING

```
<160> NUMBER OF SEQ ID NOS: 14

<210> SEQ ID NO 1
<211> LENGTH: 45
<212> TYPE: DNA
<213> ORGANISM: Artificial
<220> FEATURE:
<223> OTHER INFORMATION: 519HCStopA

<400> SEQUENCE: 1
cgcatgaaca tgctctagat gaacgattga tgagaaaaat ttctg            45

<210> SEQ ID NO 2
<211> LENGTH: 44
<212> TYPE: DNA
<213> ORGANISM: Artificial
<220> FEATURE:
<223> OTHER INFORMATION: 519HCSacB

<400> SEQUENCE: 2
gtggttggat caaagagctc accgacaatg tagtgtttca tttc             44

<210> SEQ ID NO 3
<211> LENGTH: 42
<212> TYPE: DNA
<213> ORGANISM: Artificial
<220> FEATURE:
<223> OTHER INFORMATION: 519HCSacA

<400> SEQUENCE: 3
tttgtggaga atatgagctc accaatggca acctttcgaa tg               42

<210> SEQ ID NO 4
<211> LENGTH: 51
<212> TYPE: DNA
<213> ORGANISM: Artificial
<220> FEATURE:
<223> OTHER INFORMATION: 519HCStopB

<400> SEQUENCE: 4
gacagaaatg ggctctagat gtggggtgaa tgatgatatc atcgccaaaa g     51

<210> SEQ ID NO 5
<211> LENGTH: 1372
<212> TYPE: DNA
<213> ORGANISM: Artificial
<220> FEATURE:
<223> OTHER INFORMATION: pBI-519HCF

<400> SEQUENCE: 5
aacgattgat gagaaaaatt tctggctcgg tttcaacagg gcttttttac gacacaggaa    60
accaacggat catgcgtgca catctgacat ggatgttacg atgtgtggtg aagtagcggc   120
tttggcaacc ataatcttgt tcccgtgtca taagataact tgcaacactt gcatgaacaa   180
```

```
ggtgaagggg agagtaattg acgaagttgg tgaggacttg aattgtgagc ttgaacgttt      240
acgtgaaact ctctcgtcat atggaggctc attcggtcat gtttcaacat tactcgacca      300
actgaacaaa gttttgaatg cacgtaacat gaacgatgga gcttttaaag agattgcaaa      360
gaagattgat gaaaagaaag aaagtccttg gacccacctg acagccatca ataacacgct      420
tattaaaggt tcgttagcaa ctggtaatga atttgaaaaa gcatctgata gcctgcggga      480
agttgtgagg tggcatctca aaagaacaga gtcgataaaa gctggcagtg ttgagagctt      540
cagaaacaag cgttctggaa aagctcattt caatccagct cttacgtgtg acaatcaatt      600
ggacagaaat ggcaacttct tatggggtga aagacaatat cacgccaaaa gattctttgc      660
taactacttt gaaaagattg atcacagtaa gggttatgaa tactatagtc aacgccaaaa      720
cccaaatggc attcgaaagg ttgccattgg taatttaata ttctccacaa atttggagag      780
gtttcggcag caaatggttg aacatcatat tgaccaggga ccaatcactc gagagtgtat      840 cgcactcgc aacaacaatt atgttcatgt atgtagctgc gtgaccttgg atgatggaac      900
tccagcgacg agtgaattga aaactcccac caagaatcac attgttcttg gtaattctgg      960
tgatcctaag tatgttgact tgccgactct tgagtctgat tcaatgtaca tagctaagaa     1020
aggttattgc tatatgaaca tcttttttagc gatgctcata acatacctg agaatgaggc     1080 gaaggacttt acgaagagag ttcgcgatct tgtaggttca aagcttgggg agtggccaac     1140
gatgctagat gtcgcgacat gcgccaatca attgattatc ttccatcccg atgcagccaa     1200
tgcagaactg ccgcgaattt tagtggatca ccgacagaag acaatgcacg taattgattc     1260
gtttggatct gttgattctg gatatcatat actgaaggct aacacagtta atcagttgat     1320
ccaattcgct agagaaccgc tcgatagtga aatgaaacac tacattgtcg gt             1372
```

<210> SEQ ID NO 6  
<211> LENGTH: 751  
<212> TYPE: DNA  
<213> ORGANISM: Artificial  
<220> FEATURE:  
<223> OTHER INFORMATION: pBI-519HCN

<400> SEQUENCE: 6

```
aacgattgat gagaaaaatt tctggctcgg tttcaacagg gcttttttac gacacaggaa       60
accaacggat catgcgtgca catctgacat ggatgttacg atgtgtggtg aagtagcggc      120
tttggcaacc ataatcttgt tcccgtgtca taagataact tgcaacactt gcatgaacaa      180
ggtgaagggg agagtaattg acgaagttgg tgaggacttg aattgtgagc ttgaacgttt      240
acgtgaaact ctctcgtcat atggaggctc attcggtcat gtttcaacat tactcgacca      300
actgaacaaa gttttgaatg cacgtaacat gaacgatgga gcttttaaag agattgcaaa      360
gaagattgat gaaaagaaag aaagtccttg gacccacctg acagccatca ataacacgct      420
tattaaaggt tcgttagcaa ctggtaatga atttgaaaaa gcatctgata gcctgcggga      480
agttgtgagg tggcatctca aaagaacaga gtcgataaaa gctggcagtg ttgagagctt      540
cagaaacaag cgttctggaa aagctcattt caatccagct cttacgtgtg acaatcaatt      600
ggacagaaat ggcaacttct tatggggtga aagacaatat cacgccaaaa gattctttgc      660
taactacttt gaaaagattg atcacagtaa gggttatgaa tactatagtc aacgccaaaa      720
cccaaatggc attcgaaagg ttgccattgg t                                     751
```

<210> SEQ ID NO 7  
<211> LENGTH: 751

-continued

<212> TYPE: DNA
<213> ORGANISM: Artificial
<220> FEATURE:
<223> OTHER INFORMATION: pBI-519HCC

<400> SEQUENCE: 7

```
tggggtgaat gatgatatca tcgccaaaag attctttgct aactactttg aaaagattga     60
tcacagtaag ggttatgaat actatagtca acgccaaaac ccaaatggca ttcgaaaggt    120
tgccattggt aatttaatat tctccacaaa tttggagagg tttcggcagc aaatggttga    180
acatcatatt gaccagggac caatcactcg agagtgtatc gcactgcgca acaacaatta    240
tgttcatgta tgtagctgcg tgaccttgga tgatggaact ccagcgacga gtgaattgaa    300
aactcccacc aagaatcaca ttgttcttgg taattctggt gatcctaagt atgttgactt    360
gccgactctt gagtctgatt caatgtacat agctaagaaa ggttattgct atatgaacat    420
ctttttagcg atgctcataa acatacctga gaatgaggcg aaggacttta cgaagagagt    480
tcgcgatctt gtaggttcaa agcttgggga gtggccaacg atgctagatg tcgcgacatg    540
cgccaatcaa ttgattatct tccatcccga tgcagccaat gcagaactgc cgcgaatttt    600
agtggatcac cgacagaaga caatgcacgt aattgattcg tttggatctg ttgattctgg    660
atatcatata ctgaaggcta acacagttaa tcagttgatc caattcgcta gagaaccgct    720
cgatagtgaa atgaaacact acattgtcgg t                                   751
```

<210> SEQ ID NO 8
<211> LENGTH: 1371
<212> TYPE: DNA
<213> ORGANISM: PRSV 5-19

<400> SEQUENCE: 8

```
aacgatattg ctgaaaaatt ctggctcggt ttcaacaggg ctttttttacg acacaggaaa     60 ccaacggatc atgcgtgcac atctgacatg gatgttacga tgtgtggtga agtagcggct    120
ttggcaacca taatcttgtt cccgtgtcat aagataactt gcaacacttg catgaacaag    180
gtgaagggga gagtaattga cgaagttggt gaggacttga attgtgagct tgaacgttta    240
cgtgaaactc tctcgtcata tggaggctca ttcggtcatg tttcaacatt actcgaccaa    300
ctgaacaaag ttttgaatgc acgtaacatg aacgatggag cttttaaaga gattgcaaag    360
aagattgatg aaaagaaaga aagtccttgg acccacctga cagccatcaa taacacgctt    420
attaaaggtt cgttagcaac tggtaatgaa tttgaaaaag catctgatag cctgcgggaa    480
gttgtgaggt ggcatctcaa aagaacagag tcgataaaag ctggcagtgt tgagagcttc    540
agaaacaagc gttctggaaa agctcatttc aatccagctc ttacgtgtga caatcaattg    600
gacagaaatg gcaacttctt atggggtgaa agacaatatc acgccaaaag attctttgct    660
aactactttg aaaagattga tcacagtaag ggttatgaat actatagtca acgccaaaac    720
ccaaatggca ttcgaaaggt tgccattggt aatttaatat tctccacaaa tttggagagg    780
tttcggcagc aaatggttga acatcatatt gaccagggac caatcactcg agagtgtatc    840
gcactgcgca acaacaatta tgttcatgta tgtagctgcg tgaccttgga tgatggaact    900
ccagcgacga gtgaattgaa aactcccacc aagaatcaca ttgttcttgg taattctggt    960
gatcctaagt atgttgactt gccgactctt gagtctgatt caatgtacat agctaagaaa   1020
ggttattgct atatgaacat ctttttagcg atgctcataa acatacctga gaatgaggcg   1080
aaggacttta cgaagagagt tcgcgatctt gtaggttcaa agcttgggga gtggccaacg   1140
atgctagatg tcgcgacatg cgccaatcaa ttgattatct tccatcccga tgcagccaat   1200
```

```
gcagaactgc cgcgaatttt agtggatcac cgacagaaga caatgcacgt aattgattcg    1260
tttggatctg ttgattctgg atatcatata ctgaaggcta acacagttaa tcagttgatc    1320
caattcgcta gagaaccgct cgatagtgaa atgaaacact acattgtcgg t             1371

<210> SEQ ID NO 9
<211> LENGTH: 21
<212> TYPE: DNA
<213> ORGANISM: Artificial
<220> FEATURE:
<223> OTHER INFORMATION: nptII 5' primer

<400> SEQUENCE: 9
cccctcggta tccaattaga g                                              21

<210> SEQ ID NO 10
<211> LENGTH: 16
<212> TYPE: DNA
<213> ORGANISM: Artificial
<220> FEATURE:
<223> OTHER INFORMATION: nptII 3' primer

<400> SEQUENCE: 10
ctggagttct tcgcca                                                    16

<210> SEQ ID NO 11
<211> LENGTH: 1371
<212> TYPE: DNA
<213> ORGANISM: PRSV YK

<400> SEQUENCE: 11
aacgatattg ctgaaaaatt ctggctcggt ttcaacaggg ctttcttgcg acacaggaaa     60
ccaacggatc atgtgtgcac atctgatatg gatgttacga tgtgtggtga agtagcggct    120
ttggcaacca taatcttgtt tccgtgtcat aagataactt gcaacacttg catgaacaag    180
gtaaagggga gagtaattga cgaagttggt gaggacttga attgtgaact tgaacgttta    240
cgtgaaactc tctcgtcata tggaggctca ttcggtcatg tttcaacatt actcgaccaa    300
ctgaacagag ttttgaatgc acgtaacatg aacgacggag cttttaaaga ggttgcaaag    360
aagattgatg aaagaaaga aagtccttgg acccacctaa cagccatcaa taacacgctc    420
attaaaggtt cgttggcaac tggcaatgaa tttggaaaag catctgatag cctgcgggag    480
attgtgaggt ggcatctcaa aagaacagag tcaataaaag ctggtagtgt tgagagcttt    540
agaaacaagc gttctgggaa agctcacttc aacccagctc ttacgtgcga caatcaattg    600
gacagaaatg gcaacttctt atggggtgaa agacaatatc acgccaaaag attctttgct    660
aactactttg aaaagattga tcacagtaag ggttatgagt actatagtca acgccaaaac    720
ccaaatggca ttcgaaaggt tgccattggt aatttaatat tctccacaaa tttggagagg    780
tttcgacagc aaatggttga acatcatatt gaccaggac caatcactcg cgagtgtatc    840
gcactgcgca acaacaatta cgttcatgta tgtagctgcg tcaccttaga tgatggaact    900
ccagcaacga gtgaattgaa aactcccacc aagaatcaca ttgttcttgg taattctggt    960
gatcctaagt atgttgactt gccgactctt gagtctgatt caatgtacat agctaagaaa   1020
ggttattgtt acatgaacat ctttctggcg atgctcataa acatacctga gaatgaggca   1080
aaggacttta cgaagagagt tcgcgatcta gtaggttcaa agcttgggga gtggccaacg   1140
atgctagatg tcgcgacatg cgctaatcaa ttgattatct tccatcccga tgcagccaat   1200
gcggaattgc cgcgaatttt agtggatcac cgacagaaga caatgcacgt gattgattcg   1260
```

-continued tttggatctg ttgattctgg atatcatata ctgaaggcta acacagttaa tcagttgatc 1320
cagttcgcca gagaaccgct cgatagtgaa atgaaacact acattgtcgg t 1371

<210> SEQ ID NO 12
<211> LENGTH: 1371
<212> TYPE: DNA
<213> ORGANISM: PRSV HA

<400> SEQUENCE: 12
aacgatattg ctgaaaaatt ctggcttggt tttaataggg cttttctgcg gcatagaaaa 60
ccaacggacc acacttgcac gtctgacatg gacgttacaa tgtgtgggga ggtagcagct 120
cttgcaacta taatcctgtt tccgtgccac aagataactt gcaacacttg catgagcaaa 180
gtaaagggaa gagtaattga cgaagttggt gaggatttga attgtgagct tgaacgttta 240
cgtgaaactc tttcagcata tggagggtca ttcggacatg tctcaacatt acttgatcaa 300
ttaaacagag ttttgaatgc gcggaacatg aacgatggag cttttaaaga gattgcgaag 360
aagattgatg aaaagaaaga gagtccttgg actcacatga caaccatcaa caacacgctc 420
tacaaaggtt cgttagcaac tggctacgaa tttgagagag catctaatag tctccgagag 480
atcgttagat ggcacctcaa aaggacagaa tcaataaaag ctggcagcgt tgaaagtttt 540
agaaataagc gttctgggaa agctcacttc aacccagctc ttacgtgtga taatcagttg 600
gataagaatg gtaatttctt atggggtgaa aggcagtacc acgctaaaag attctttgcc 660
aactattttg agaagattga tcatagtaag ggttatgagt actatagtca acgccaaaac 720
ccaaatggta tcaggaaaat tgccattggt aatttggtat tttcaacaaa tttggagaga 780
tttcggcagc aaatggttga acaccatatt gatcaaggac caattactcg tgagtgcatt 840
gcattgcgta ataacaatta cgtccatgta tgtagctgcg taactttaga tgatggaact 900
ccagcgacaa gtgagttgaa aactcctacc aagaatcaca tcgttcttgg taattctggt 960
gatcctaagt acgttgacct gccgactctt gagtctgatt cgatgtacat agctaaaaag 1020
ggttattgct acatgaacat ttttttagct atgctcataa acatacctga aaatgaggcg 1080
aaggacttca caaaaagggt tcgtgacctt gtgggttcaa aacttggaga gtggccaacg 1140
atgctagatg tcgcaacatg cgcaaatcag ctggtagttt ttcatcctga cgcagccaac 1200
gcagaattac cgcaaattct agtggatcac cgacagaaaa caatgcatgt catcgattct 1260
tttgggtccg tggattctgg atatcatata ttgaaggcaa atacagtcaa tcagctgatc 1320
caattcgcta gggacccact cgatagtgaa atgaagcact acattgtcgg c 1371

<210> SEQ ID NO 13
<211> LENGTH: 1371
<212> TYPE: DNA
<213> ORGANISM: PRSV TH

<400> SEQUENCE: 13
aacgatattg ccgaaaaatt ctggcttggt ttcaacaggg ctttcttgaa gcataggaag 60
ccaacggatc atgtgtgcac atctgacatg gatgttacaa tgtgcggtga agtagcggct 120
ctagcgacca taatcttgtt tccgtgtcat aaaataactt gcaacacatg catgaacagg 180
gtcaaggaga gagttattga cgaagttggt gaggacttaa attgtgagct cggacgttta 240
cgtgaaaccc tctcgtcata tggaggctca tttggccatg tttcaacgtt acttgatcaa 300
ttgaacagag ttttgaatgc gcgaaacatg aacgatggag cttttaaaga gattgcgaag 360
aagattgacg agaagaaaga aagtccttgg acccacatga catttatcaa taatacgctt 420

```
attaaaggtt ctttggcaac tggccatgaa tttgaaagag cgtctgatag tctgcgagaa      480
gttgtgagat ggcatctcaa aaggacagaa tcgataaaag ctggcagtgt tgagagcttc      540
agaaacaaac gttctggaaa agctcacttc aacccagctc tcacgtgtga caatcaattg      600
gacagaaacg gcaatttctt atggggtgag agacagtatc acgctaaaag attctttgct      660
aactactttg agaagattga tcacagtaag ggctatgagt actacagtca gcgccaaaac      720
ccaaatggta ttcgaaagat cgccattggt aatctaatct tttccacaaa tttggagagg      780
tttcggcagc aaatgattgg acattacatt gaccagggac caatcactcg tgagtgcatc      840
gcactgcgca ataataatta cgttcatgta tgtagttgcg tgaccttaga tgatggaact      900
ccagcgacaa gtgaattaaa aactcctacc aagaatcaca ttgttcttgg taatgccggt      960
gatcctaagt atgttgactt accgactctt gagtctgatt caatgtacat agctaagaaa     1020
ggttactgct acatgaacat ctttctggcg atgctcataa acatacctga gaatgaggcg     1080
aaggacttta cgaagagagt tcgtgatctt gtaggttcaa aacttgggga atggccgacg     1140
atgttagatg tcgcgacatg cgcaaatcaa ttgattatct ttcatcccga tgcagccaat     1200
gcggaattgc cgcgaatcct cgttgatcac cgacagaaaa caatgcatgt cattgattcg     1260
tttggatccg tggattctgg ataccatata ctgaaggcga acacagtaaa tcagttgatt     1320
cagttcgcca gagagccgct cgatagtgaa atgaaacact acattgtcgg c              1371
```

<210> SEQ ID NO 14
<211> LENGTH: 1371
<212> TYPE: DNA
<213> ORGANISM: PRSV MX

<400> SEQUENCE: 14

```
aacgatattg ctgaaaaatt ctggctcggt ttcaataggg cttttctacg gcatagaaag       60
ccaacggacc acacttgcac gtctgacctg gaagttacga cgtgtgggga ggtagcagcg      120
cttgcaacta taatcctgtt tccgtgtcac aaaataactt gcaacacttg catgagtaaa      180
gcaaagggaa gagttattga tgaagttggt gaggacttga attgtgaact tgaacgtttg      240
cgtgaaactc tttcatcata tggagggtca ttcggacatg tctcaacatt gcttgatcaa      300
ctaaacagag ttttaaacgc gcgaaacaca aacgatggag cttttaaaga gattgcgaaa      360
aagatcgatg caaagaaaga gagtccttgg actcacatga caaccatcaa caacacgctc      420
atcaaaggtt cgctagcaac tggttacgaa ttcgaaagag cgtctgatag tcttctagag      480
attgtgagat ggcatctcaa aaggacagaa tcaataaaag ctggcagtgt tgaaagtttt      540
agaaataagc gttctggaaa agctcacttt aacccagctc taacgtgtga taatcagttg      600
gacaggaatg gtaatttctt atggggtgaa aggcaatacc acgccaaaag attctttgcc      660
aattatttcg agaagatcga tcatagcaag ggttatgagt actatagcaa cgccaaaac      720 ccaaatggcg tcaggaaaat tgccattggt aatttagtat tttcaacaaa tttggaagaga      780 tttcggcagc aaatggttga acaccacatt gatcaaggac caattactcg cgagtgcatc      840
gcattgcgca ataacaatta tgttcatgta tgtagctgtg taactttgga tgacggaact      900
ccagcaacaa gtgagttgaa gactcctacc aagaatcaca ttgttcttgg taattctggt      960
gatcctaagt acgttgacct gcctactctt gagtctgatt caatgtacat agccaaaagg     1020
ggttattgct acatgaatat atttttagcg atgctcataa atatacctga gaatgaggca     1080
aaggacttca caaagagagt tcgcgaccta gtgggttcaa aacttggaga atggccaacg     1140
atgttggatg ttgcaacatg tgcaaatcag ctggtaatct ttcatcctga tgcggccaac     1200
```

```
gcagaattgc cgcgaattct agtggaccac cgacagagga cgatgcatgt cattgactct    1260
tttgggtccg tggattctgg gtatcatata ttgaaggcaa acacagttaa tcagctgatt    1320
caattcgcta gagaaccact cgatagtgaa atgaaacact acattgttgg t             1371
```

GENE-TRANSFER VECTOR COMPRISING HELPER-COMPONENT PROTEASE GENE OF PAPAYA RINGSPOT VIRUS FOR BROAD-SPECTRUM VIRUS RESISTANCE IN CROPS AND USE THEREOF

BACKGROUND OF THE INVENTION

1. Field of the Invention

The present invention relates to a recombinant plasmid for providing plants with resistance against virus having a coding sequence fragment of Papaya ringspot virus helper-component protease gene (PRSV HC-Pro gene). The present invention also relates to a recombinant microorganism. The present invention also relates to a method for providing plants with resistance against virus. The present invention also relates to use of full length or fragment of helper-component protease in manufacturing a plant with resistance to virus.

2. Description of the Prior Arts

*Carica papaya* L. is one of the high value crops. Effective cures for its virus infection have not been established. Based on progress of plant tissue culture techniques, breakthrough of plant transforming techniques and the concept of pathogen-derived resistance, transferring a portion of viral genome into chromosome of a plant host recently has become a popular means for providing plants with resistance against virus. Transgenic papaya lines were obtained by transforming papaya with the CP gene of PRSV Hawaii strain by microprojectile bombardment (Fitch et al., 1992), but they are not resistant to Taiwan PRSV YK isolate, due to sequence homology-dependent resistance. This limits the application of those transgenic papaya lines in other geographic regions.

Transgenic papaya lines carrying the CP gene of Taiwan PRSV YK isolate were generated by *Agrobacterium*-mediated transformation (Cheng et al., 1996). Through inoculation of virus and evaluation, the transgenic papaya lines were proven as conferring high level of broad spectrum resistance to PRSV YK as well as distinct PRSV strains from various geographical regions including Hawaii (HA), Mexico (MX) and Thailand (TH) (Bau et al., 2003). YK coat protein transgenic papaya lines confer high levels of resistance to PRSV (Bau et al., 2004). Resistance of transgenic plants carrying coat protein transgene is mediated by the mechanism of post-transcriptional gene silencing (PTGS), PRSV RNA genome is degraded, resulting in achieving resistance against virus. However, the conventional means for providing viral resistance to crops is based on sequence homology. Therefore, a common problem of the conventional means resides in the resistance is virus strain specific (Tennant et al., 2001). Conventional transgenic papaya lines carrying coat protein gene from various virus strains have limited applications in certain geographical regions.

Applicants have generated PRSV YK CP transgenic lines with different levels of resistance to Taiwan PRSV YK strain by introducing coat protein of PRSV YK into premature embryo through *Agrobacterium*-mediated transformation (Cheng et al., 1996) and selecting out lines with high levels of resistance to virus from various geographical regions such as Hawaii (HA), Thailand (TH) and Mexico (MX) (Bau et al., 2003). The obtained transgenic lines carrying PRSV YK CP gene are subjected to field trials and proven having high levels of resistance to PRSV (Bau et al., 2004).

During the field trials, transgenic resistance of PRSV YK CP transgenic papaya lines is found to be broken down by Papaya ringspot virus super strain. Breakdown of the resistance mediated by coat protein gene is suggested to be caused by helper-component protease (HC-Pro). HC-Pro is known as a gene silencing suppressor, capable of repressing post-transcriptional gene silencing (Anadalakshmi et al., 1998; Brigneti et al., 1998; Shi et al., 1997). Applicants suggest that PRSV 5-19 HC-Pro can suppress gene-silencing mechanism of PRSV YK CP transgenic papaya line. According to failure of using coat protein transgene alone in protecting plants from attacks by super virus strain, a new strategy is developed by the applicants.

SUMMARY OF THE INVENTION

Transgenic resistance of coat protein transgenic plants is homology-dependent, resulting in resistance that can be broken down by PRSV super strain carrying super gene silencing suppressor HC-Pro. Therefore, the main objective of the present invention is to provide a transgenic plasmid and use thereof through a strategy of inserting HC-Pro gene in a binary vector as a untranslatable construct; wherein post-transcriptional gene silencing of resulting transgenic plants is activated to prevent the transgenic plants themselves from being broken down by virus. The transgenic plants have broad-spectrum of resistance to virus and are competent to resist viruses from different origins or geographical regions. Thus, technical solution for resolving the breakdown of coat protein transgenic papaya lines by PRSV super strain is provided.

In one aspect, the present invention provides a recombinant plasmid, comprising a control sequence and a coding sequence fragment of Papaya ringspot virus helper-component protease gene (PRSV HC-Pro gene) operably linked to the control sequence.

In another aspect, the present invention provides a recombinant microorganism prepared by transforming a microorganism with the recombinant plasmid as described above.

In another aspect, the present invention provides a method for providing plant with resistance against virus, comprising steps of: introducing the recombinant plasmid as described above into a plant or plant part to allow the plant or plant part not translationally expressing transcripts of the coding sequence fragment of the Papaya ringspot virus helper-component protease gene without expressing helper-component protease, whereby the plant or plant part has resistance against virus through post-transcriptional gene silencing.

In yet another aspect, the present invention provides a recombinant plant cell, comprising a genome containing a sequence selected from the group consisting of: sequences having 85% homology with sequence set forth in SEQ ID NO: 5, having 85% homology with sequence set forth in SEQ ID NO: 6 and having 85% homology with sequence set forth in SEQ ID NO: 7.

In yet another aspect, the present invention provides use of full-length Papaya ringspot virus helper-component protease gene or fragment thereof in generating a plant with resistance against virus, comprising: providing a full-length Papaya ringspot virus helper-component protease gene or fragment thereof; and introducing the full length Papaya ringspot virus helper-component protease gene or fragment thereof into a plant or plant part to obtain a plant or plant part with resistance against virus.

Based on the aforesaid, HC-Pro gene is used as a target gene for attacking virus, which provides a broad-spectrum of resistance to various virus strains of various geographical origins and solves the problem of homology-dependent resistance, such that resulting transgenic plants have great value for agricultural application.

BRIEF DESCRIPTION OF THE DRAWINGS

FIG. 2 illustrates comparison between symptoms of highly resistant 5-19 HC-Pro transgenic papaya line F3-2-2 after inoculation with PRSV 5-19 and PRSV YK;

Figure 5A:
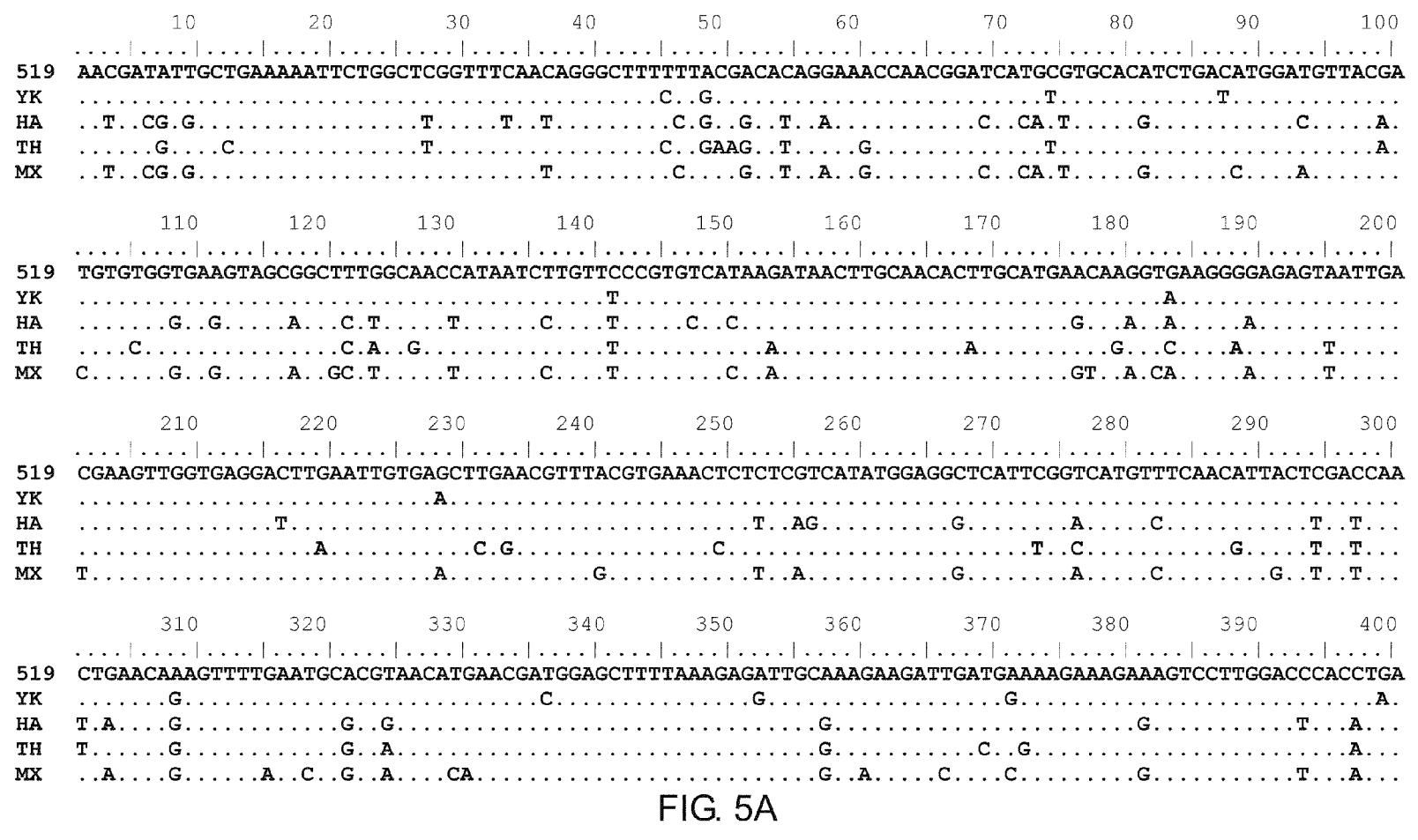
Figure 5B:
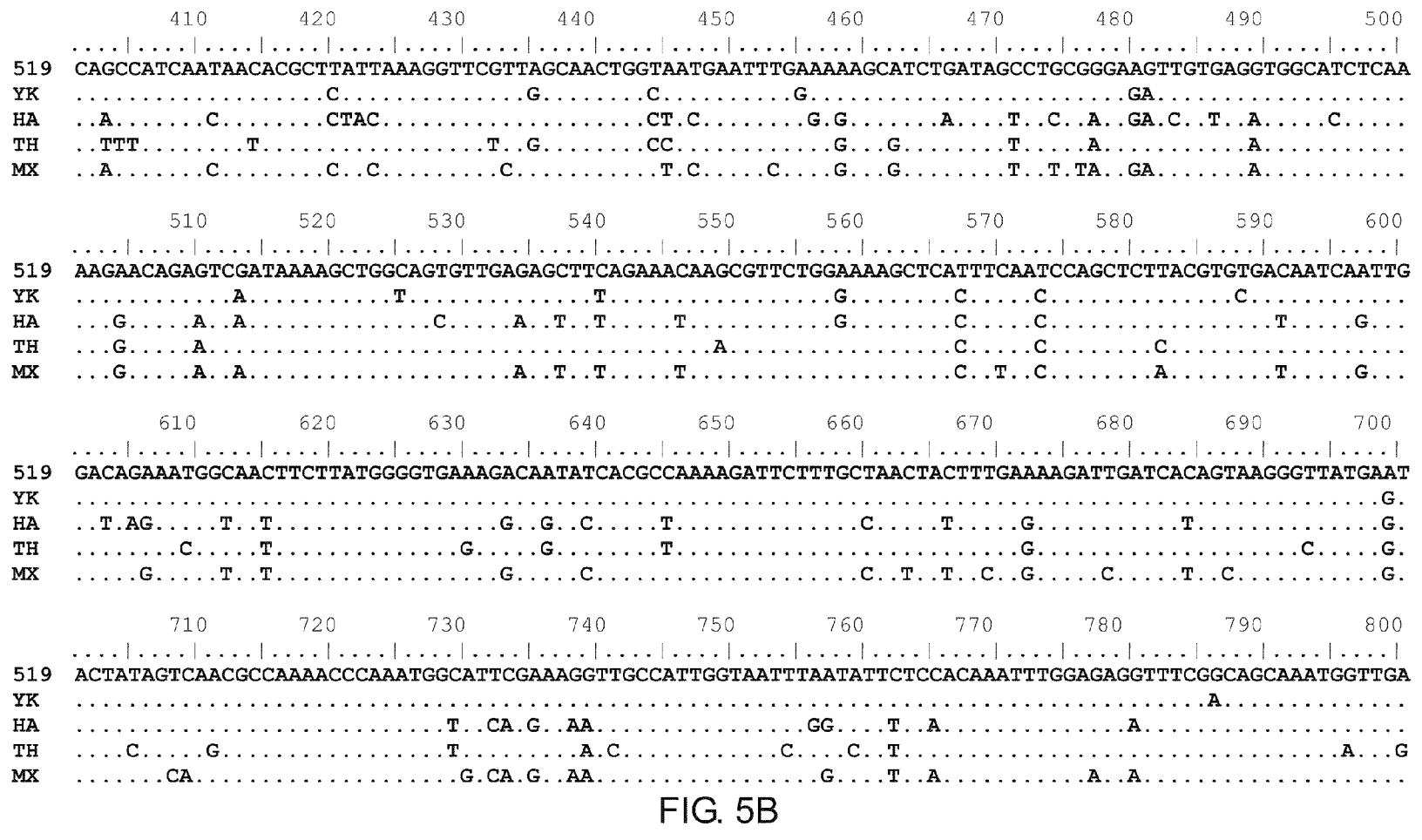
Figure 5C:
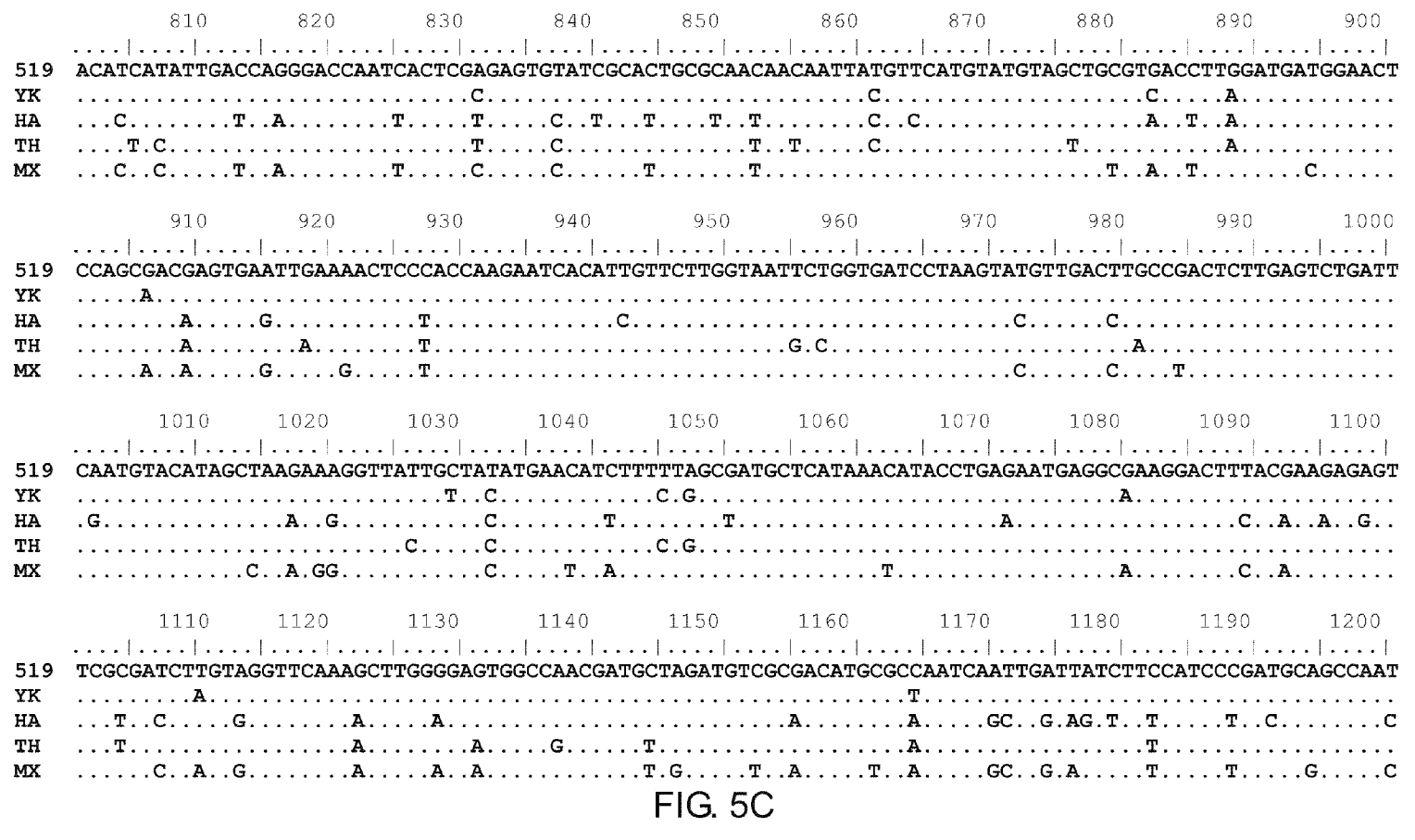

FIGS. 5A to 5D illustrate alignment of nucleic sequences of HC-Pro genes of Papaya ringspot virus strains as indicated, wherein "." represent identical nucleic acids in the sequences, and symbols YK, HA, TH and MX respectively represent SEQ ID NOs 11, 12, 13 and 14.

DETAILED DESCRIPTION OF THE PREFERRED EMBODIMENTS

Figure 1:
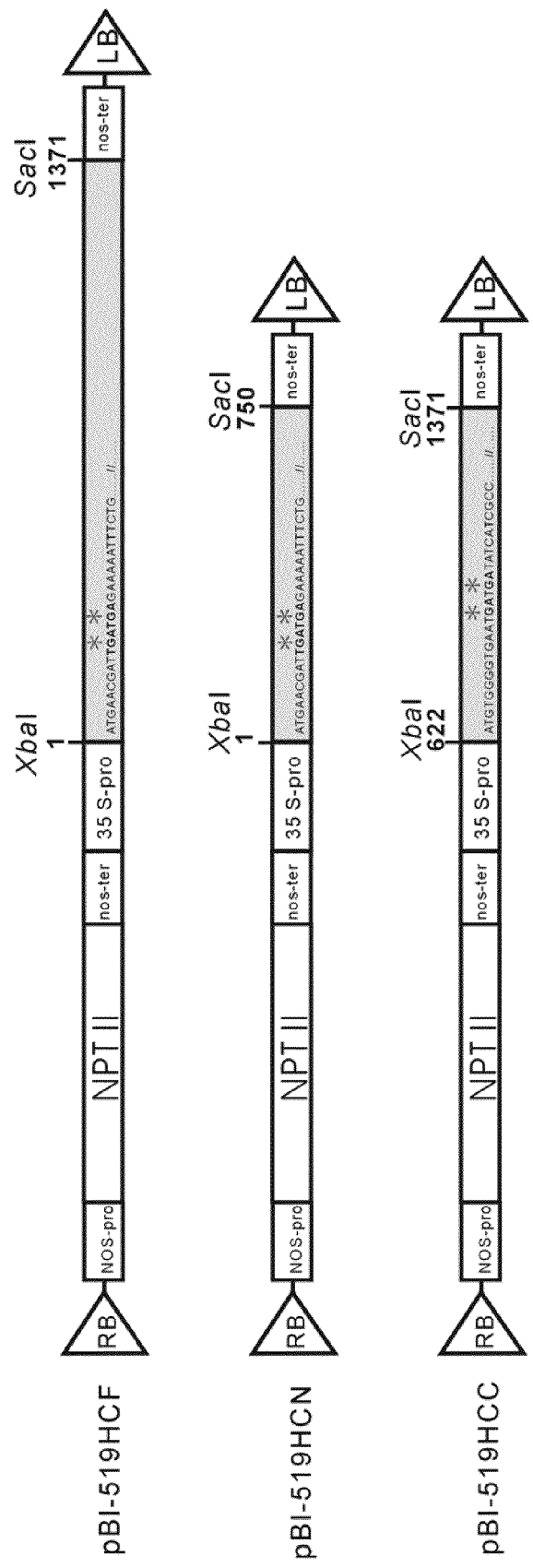
FIG. 1 illustrates a schematic diagram of pBI-519HCF, pBI-519HCN and pBI-519HCC, untranslatable constructs of full-length PRSV 5-19 helper-component protease (HC-Pro) gene or fragment thereof.

A recombinant plasmid in accordance with the present invention comprises a control sequence and a coding sequence fragment of Papaya ringspot virus helper-component protease gene (PRSV HC-Pro gene) operably linked to the control sequence.

According to the present invention, Papaya ringspot virus helper-component protease gene is a gene silencing suppressor capable of repressing post-transcriptional gene silencing (PTGS) (Anadalakshmi et al., 1998; Brigneti et al., 1998; Shi et al., 1997).

According to the present invention, the coding sequence fragment of Papaya ringspot virus helper-component protease gene is constructed into a plasmid to be untranslatably expressed by any processes as known in the art, for example, but not limited to: placing the coding sequence fragment downstream of the control sequence, and providing at least one stop codon, preferably, multiple stop codons and more preferably, two consecutive stop codons, at the 5' end of the coding sequence.

According to the present invention, the full-length Papaya ringspot virus helper-component protease gene has a sequence set forth in SEQ ID NO: 8.

According to the present invention, the term "operably linked" refers to expression of a gene controlled by a spatially linked control sequence. The control sequence may be at 5' end (upstream) or 3' end (downstream) of the gene controlled by the control sequence. As known in the art, distance between control sequence and the gene can be adjusted without influencing function of the control sequence. According to the present invention, "coding sequence" refers to a region in a gene transcribed into messenger RNA (mRNA) and translated into protein. The "coding sequence fragment" refers to full-length or part of the region.

According to the present invention, the term "homology" refers to degree of similarity between two sequences, which is determined by identical and/or conservative ratio between the sequences.

The term "control sequence", as used herein, refers to a sequence capable of switching on or off a gene or fragment thereof to regulate expression of the gene or fragment thereof, such as a promoter or terminator.

According to the present invention, the control sequence may be any promoters adapted to control expression of HC-Pro transgene in accordance with the present invention, for example, but not limited to: 35S promoter. The control sequence may be any compatible in plants, for example, but not limited to: Cauliflower mosaic virus 35S promoter (CaMV 35S promoter).

According to the present invention, the coding sequence fragment may be modified by any means to prevent expression of protein corresponding to the coding sequence fragment; and preferably, by inserting a stop codon at 5' end or including a reading frame shift.

According to the present invention, the coding sequence fragment has a nucleotide sequence selected from the group consisting of: (i) a nucleotide sequence having at least 85% homology with sequence set forth in SEQ ID NO: 5; (ii) a nucleotide sequence with at least 85% homology with sequence set forth in SEQ ID NO: 6.; and (iii) a nucleotide sequence with at least 85% homology with sequence set forth in SEQ ID NO: 7.

According to the present invention, the recombinant plasmid further comprises resistant gene being any antibiotic resistant gene or selection gene, for example, but not limited to: nptII gene, a kanamycin resistant gene.

According to the present invention, the recombinant plasmid may be obtained by inserting Papaya ringspot virus helper-component protease gene into a binary vector, wherein the binary vector includes promoter or terminator compatible to plants, for example, but not limited to: pBI121 and derivatives thereof. As known in the art, the binary vector refers to a cloning vector for generating a transgenic plant, having ability to be amplified in *Escherichia coli* and *Agrobacterium tumefaciens*, may have a CaMV 35S promoter and a Nos terminator. Preferably, the coding sequence fragment is located between CaMV 35S promoter and Nos terminator.

In a preferred embodiment of the present invention, the recombinant plasmid in accordance with the present invention is pBI-519HCF, which is deposited as an *E. coli* transformant in China Center for Type Culture Collection under CCTCC accession number CCTCC M 2010112.

In another preferred embodiment in accordance with the present invention, the recombinant plasmid in accordance with the present invention is pBI-519HCN or pBI-519HCC, which may be obtained by polymerase chain reaction in combination with cloning techniques in the art by using pBI-519HCF as template and a primer pair, such as, 519HCStopA (SEQ ID NO: 1) and 519HCSacA (SEQ ID NO: 3), or 519HCStopB (SEQ ID NO: 4) and 519HCSacB (SEQ ID NO:2), or by enzyme digestion in combination with cloning.

A recombinant microorganism in accordance with the present invention is prepared by transforming a microorganism with the recombinant plasmid as described above, wherein the microorganism preferably is bacterium; and more preferably, disarmed *Agrobacterium tumefaciens*.

According to the present invention, said disarmed *Agrobacterium tumefaciens* refers to *Argrobacterium tumefaciens* containing vir genes and T-DNA, but no oncogenes of *Agrobacterium* sp.

A method for providing plant with resistance against virus in accordance with the present invention comprises steps of: introducing the recombinant plasmid as described above into a plant or plant part to allow the plant or plant part not translationally expressing transcripts of the coding sequence fragment of the Papaya ringspot virus helper-component protease gene without expressing helper-component protease, whereby the plant or plant part has resistance against virus.

According to the present invention, the terms "introduce" and "transfer" are alternatively used and refer to bringing a nucleic acid fragment, plasmid and the like into cells by any known transformation techniques in the art.

According to the present invention, the step of introducing the recombinant plasmid as described above into a plant or plant part, as known in the art, includes use of, for example, but not limited to: *Agrobacterium* sp, microprojectile bombardment, electroporation, microinjection and sonication.

According to the present invention, the term "untranslational expression" or "not translationally expressed" refers to allow a gene being expressed before the stage of gene translation by any means, that is, no complete protein is expressed. Therefore, means therefor may include providing a coding sequence fragment having a reading frame shift or inserting a stop codon into the coding sequence fragment, which results in producing transgene transcripts but not proteins of the transgene. Since the transcripts will be degraded into small interfering RNA (siRNA), no transgene transcripts but a great amount of fragments of siRNA are detected in resulting transgenic lines with resistance against virus.

According to the present invention, the plant is selected from the group consisting of: plants belonging to Cucurbitaceae and Caricaceae. Preferably, the plant or plant part is derived from *Carica papaya* L. and includes root, stem, leaf or embryo.

According to the present invention, the step of introducing the recombinant plasmid as described above into a plant or plant part includes: introducing the recombinant plasmid into a *Agrobacterium* sp. to obtain a recombinant *Agrobacterium* sp.; and infecting the plant or plant part with the recombinant *Agrobacterium* sp. to obtain a plant having the coding sequence fragment.

The present invention provides a use of full-length Papaya ringspot virus helper-component protease gene or fragment thereof in generating a plant with resistance against virus.

Preferably, the full-length Papaya ringspot virus helper-component protease gene has a sequence set forth in SEQ ID NO: 8. More preferably, the full-length Papaya ringspot virus helper-component protease gene or a fragment thereof has a sequence selected from the group consisting of: sequences (i) having 85% homology with sequence set forth in SEQ ID NO: 5; (ii) having 85% homology with sequence set forth in SEQ ID NO: 6; and (iii) having 85% homology with sequence set forth in SEQ ID NO: 7.

Preferably, the method for using a full-length Papaya ringspot virus helper-component protease gene or fragment thereof in generating a plant with resistance against virus in accordance with the present invention comprises: introducing an untranslatable construct containing a full-length Papaya ringspot virus helper-component protease gene or fragment thereof into a plant or plant part.

According to the present invention, the untranslatable construct is generated by cloning a full-length Papaya ringspot virus helper-component protease gene or fragment thereof into an expression plasmid without expressing Papaya ringspot virus helper-component protease. The untranslatable construct exerts its function through expressing RNA in the plant in conjunction with gene silencing mechanism within the plant to achieve the objective of providing plant with resistance against Papaya ringspot virus, which contains essentially identical helper-component protease.

Preferably, the untranslatable construct is a binary vector containing an insertion of a full-length Papaya ringspot virus helper-component protease gene or fragment thereof, wherein the full-length Papaya ringspot virus helper-component protease gene or fragment thereof has a stop codon and reading frame shift.

A recombinant plant cell in accordance with the present invention comprises a genome containing a sequence selected from the group consisting of: sequences having 85% homology with sequence set forth in SEQ ID NO: 5, having 85% homology with sequence set forth in SEQ ID NO: 6 and having 85% homology with sequence set forth in SEQ ID NO: 7. Preferably, the recombinant plant cell in accordance with the present invention comprises a genome containing a sequence selected from the group consisting of: sequences having 90% homology with sequence set forth in SEQ ID NO: 5, having 90% homology with sequence set forth in SEQ ID NO: 6 and having 90% homology with sequence set forth in SEQ ID NO: 7.

Preferably, the recombinant plant cell is produced by transforming a plant cell with a recombinant plasmid as described above or a recombinant microorganism as described above. More preferably, the plant cell is derived from a plant callus or a somatic embryo.

The present invention was further illustrated by the following examples; it should be understood that the examples and embodiments described herein are for illustrative purposes only and should not be construed as limiting the embodiments set forth herein.

EXAMPLES

1. Construction of Untranslatable Constructs of HC-Pro Gene

The HC-Pro coding sequence (SEQ ID NO: 8) of PRSV 5-19 were amplified by reverse-transcriptase polymerase chain reaction (RT-PCR) using specific primers (519HCStopA and 519HCSacB) and the amplified product was cloned into pCRII-TOPO® vector (Invitrogen). The forward primer 519HCStopA [5'-CGCATGAACATGC TCTAGATGAACGATTGATGAGAAAAATTTCTG-3' (SEQ ID NO: 1) containing two stop codons (in bold), an XbaI site (underlined) and an extra nucleotide inserted to create frame-shift (in bold)], and the reverse primer 519HCSacB [5'-GTGGTTGGATCAAA GAGCTCACCGACAATGTAGTGTTTCA TTTC-3' (SEQ ID NO: 2) with SacI site (underlined)] were used to amplify the frame-shifted full-length HC-Pro (1371 bp) coding sequence with two upstream stop codons (SEQ ID NO: 5) by PCR. The amplified fragment was digested with XbaI/SacI and ligated to XbaI/SacI digested pBI121 (Clontech, CA) vector to generate the untranslatable construct "pBI-519HCF" as shown in FIG. 1 (containing two stop codons as indicated with "**" and a nucleotide T in bold) and the construct was affirmed by sequencing and ready for use.

The primer 519HCStopA (SEQ ID NO: 1) and 519HCSacA [5'-TTTGTGGAGAATAT GAGCTCACCAATGGCAACCTTTCGAATG-3' (SEQ ID NO: 3) with SacI site (underlined)] were used for amplifying the N-terminal fragment (750 bp) of the HC-Pro gene. The fragment was digested with XbaI/SacI and then ligated to XbaI/SacI digested pBI121 vector to generate the untranslatable construct "pBI-519HCN" as shown in FIG. 1 (containing two stop codons as indicated with "**" and a nucleotide T in bold) and the construct was affirmed by sequencing and ready for use.

The primer 519HCStopB [5'-GACAGAAATGGGC TCTAGATGTGGGGT GAATGATGATATCATCGC-CAAAAG-3' (SEQ ID NO: 4) with two stop codons (in bold), an XbaI site (underlined) and an inserted extra nucleotide (in bold)] and primer 519HCSacB (SEQ ID NO: 2) were used for amplification of the C-terminal fragment (750 bp) of HC-Pro gene. The fragment was digested with XbaI/SacI and then ligated to XbaI/SacI-digested pBI121 vector to generate the untranslatable construct "pBI-519HCC" as shown in FIG. 1

(containing two stop codons as indicated with "**" and a nucleotide T in bold) and the construct was affirmed by sequencing and ready for use.

The three untranslatable constructs containing the full HC-Pro gene, N-terminal half of HC-Pro gene, and C-terminal half of HC-Pro gene were transferred into *Agrobacterium tumefaciens* LBA4404 (Invitrogen) by electroporation to obtain transformed *Agrobacterium tumefaciens* containing untranslatable chimera and ready for transformation of papaya.

2. Generation of Transgenic Papaya Lines

Papaya transformation and regeneration were carried out following the method described recently (Kung et al. 2009) with modifications. For *Agrobacterium*-mediated transformation, shoots derived from known characterized *Carica papaya* cv. were used and cultured in vitro in a laboratory tissue culture system. The shoots were cultured in Murashige-skoog medium containing 0.02 mg/l α-naphthaleneacetic acid and 0.2 mg/l benzylaminopurine (MSNB) for two weeks, followed by being transferred to MS medium containing Indole-3-butyric acid (IBA) and cultured at dark at 28° C. for one week to induce generation of root primordium, as root induction period (auxin dependent); and being transferred to pearlite containing ½ volume of MS to allow root elongating, as root development period (auxin independent). After two weeks, tips of the roots were cut off and cultured in MS medium containing 1 mg/l 2,4-dichlorophenoxyacetic acid and 0.1 mg/l benzylaminopurine (MSDB medium) to induce growth of culli and somatic embryos to obtain somatic embryos of the *Carica papaya* cv.

In the following examples, the somatic embryos from adventitious roots of the papaya line Sunrise were wounded by carborundum in distilled water for 1 min (Cheng et al., 1996). The wounded somatic embryos were mixed and submerged in the culture of *A. tumefaciens* with various constructs as described above for 5 min. The treated somatic embryos were transferred to the medium containing 5 mg/l 2,4-dichlorophenoxyacetic acid (2-4D) and co-cultivated for two days and then washed with distilled water to remove excess *A. tumefaciens*. The treated somatic embryos were subcultured on medium containing 500 mg/l carbenicillin and 5 mg/l 2-4D for two weeks and further subcultured on the same medium with 50 mg/l kanamycin for selection, followed by selection with 100 mg/l kanamycin for two months. The selected tissues were then nursed on medium without kanamycin for embryo development for a month for transformed somatic embryos recovering ability of regeneration. The transformed somatic embryos were then germinated on the MSNB medium containing 50 mg/l kanamycin for shoot development, as "putative transgenic papaya lines".

3. Detecting Putative Transgenic Papaya Lines by Polymerase Chain Reaction

The genomic DNA was extracted from plantlets of putative transgenic papaya lines. The plasmid DNA of pBI-519HCF, pBI-519HCN and pBI-519HCC were used as positive controls for polymerase chain reaction (PCR) in combination with the primer pairs 519HCStopA/519HCSacB, 519HCStopA/519HCSacA, and 519HCStopB/519HCSacB to amplify HC-Pro full-length gene, N-terminal fragment and C-terminal fragment, respectively. Additionally, nptII 5' primer 5'-CCCCTCGGTATCCAATTAGAG-3' (SEQ ID NO: 9) and nptII 3' primer 5'-CTGGAGTTCTTCGCCA-3' (SEQ ID NO: 10) were used in PCR to amplify nptII gene for determining the presence of a predetermined fragment by gel electrophoresis, whereby transformed plantlets were identified. The results confirmed that 15 lines contained HC-Pro full-length gene, 31 lines contained HC-Pro N-terminal gene fragment and 14 lines contained HC-Pro C-terminal gene fragment.

4. Evaluation of Resistances of Transgenic Papaya Lines

The sixty obtained transgenic papaya lines were micropropagated and evaluated for their resistance against virus in a greenhouse. Plantlets of each line were mechanically inoculated with super strain PRSV 5-19 isolate or PRSV YK isolate. Seven weeks after inoculation, the lines without symptoms and with high levels of resistance against virus were selected out, wherein responses of the lines against virus were classified into three categories as follows:

(1) Susceptible lines (S): which showed severe symptoms of mosaic on leaves 14 days after inoculation;

(2) Delayed-type resistant line (DR): which showed a one- to two-week delay in symptom development as compared to that of non-transgenic papaya line (NT); and (3) Highly resistant line (HR): which showed no symptoms 28 days after inoculation.

Figure 2:
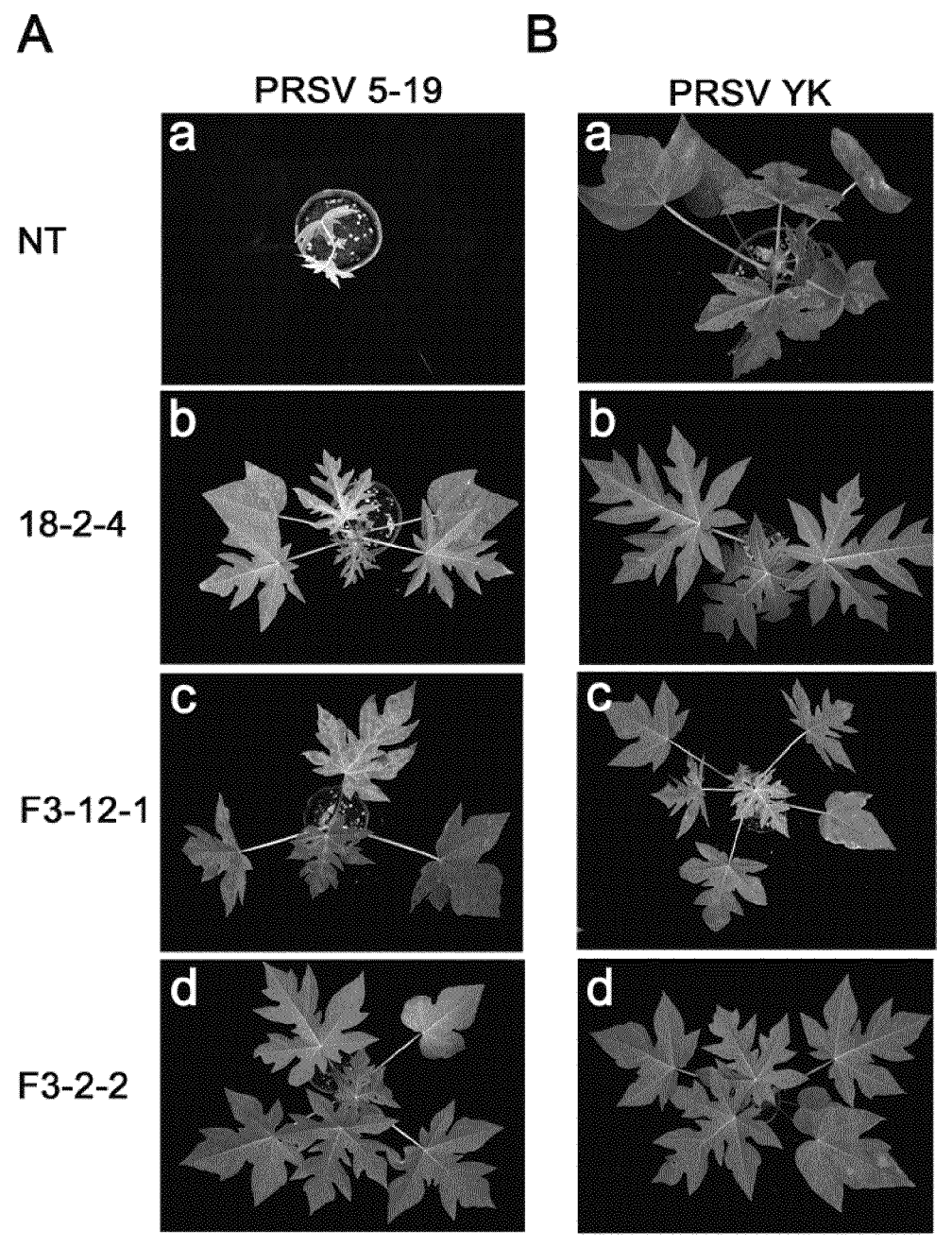

As shown in FIG. 2, plantlets of the sixty transgenic lines, including highly resistant line F3-2-2, susceptible line F3-12-1, 18-2-4 (YK-CP transgenic line) and non-transgenic line, were inoculated with PRSV 5-19 and PRSV YK viruses and evaluated after four weeks. The symptoms of F3-2-2, F3-12-1, 18-2-4 (YK-CP transgenic line) and non-transgenic line (NT) that were inoculated with PRSV 5-19 were illustrated in panel A in FIG. 2, wherein the control group NT showed wilting symptom on leaves (A-a, which represented column a in panel A of FIG. 2; and so forth); and the other control group, PRSV YK-CP transgenic papaya line 18-2-4, also showed severe symptom of mosaic leaves (FIG. 2 A-b). While, the control group 18-2-4 inoculated with PRSV YK showed great resistance against PRSV YK (FIG. 2, B-b).

Results of evaluation of the sixty transgenic lines were shown in Table 1, wherein thirty one transgenic papaya lines (4 lines from pBI-519HCF, 20 lines from pBI-519HCN and seven lines from pBI-5-19HCC) showed vein-clearing and mosaic symptoms on newly emerged leaves.

The thirty one transgenic papaya lines of the sixty transgenic lines were classified as susceptible (S) lines, such as F3-12-1 as shown in FIG. 2, A-c; thirty of thirty one PRSV 5-19 susceptible lines (S) were also susceptible to PRSV YK (S), showing severe symptoms of vein-clearing and leaf-mosaic, similar to symptoms on inoculated NT control plants (FIG. 2, B-a and -c) and were classified as susceptible lines (S) to YK. One line (N10-3-1) was susceptible to PRSV 5-19 but had delayed-resistance to PRSV YK and classified as delayed-type resistant line (DR).

Ten lines of the sixty transgenic lines showed one to two weeks delay in symptom development when inoculated with PRSV 5-19 and were classified as delayed-type resistant (DR) lines. The seven of these ten lines also showed delayed-type resistance to PRSV YK, while the other three lines showed high levels of resistance to PRSV YK (HR).

The remaining nineteen lines over total sixty transgenic lines, which did not show any symptoms after being inoculated with PRSV 5-19 (FIG. 2A-d) or PRSV YK (FIG. 2B-d), were classified as highly resistant (HR) lines. During the 7-week observation period, a total of 23 transgenic HR lines remained symptomless to PRSV YK and 19 lines of these 23 lines remained symptomless to PRSV 5-19.

As shown in Table 1, seven of fifteen pBI-5-19HCF transgenic lines (46.6%) were highly resistant against PRSV 5-19 and YK, as no disease incidence was noticed 28 days after inoculation with each virus, nine of thirty-one pBI-5-19HCN transgenic lines (29.0%) showed high resistance against both virus strains, and three of fourteen pBI-5-19HCN transgenic lines (21.4%) showed high resistance against both viruses. The results indicated that all three constructs provided high degrees of resistances against Papaya ringspot virus super stain PRSV 5-19 and typical PRSV YK strain.

TABLE 1

Evaluation of the resistance of 5-19 HC-Pro transgenic papaya lines against PRSV 5-19 or PRSV YK

| Constructs | No. of as-sayed lines | Response after challenge[a] with [Numbers of lines (percentage in total lines %)] | | | | | |
|---|---|---|---|---|---|---|---|
| | | PRSV 5-19 | | | PRSV YK | | |
| | | Highly resistant[c] (HR %) | Re-sis-tant | Sus-cep-tible | Highly resistant (HR %) | Re-sis-tant | Sus-cep-tible |
| pBI-519HCF | 15 | 7 (46.6) | 4 | 4 | 8[d] (53.3) | 3 | 4 |
| pBI-519HCN | 31 | 9 (29.0) | 2 | 20 | 11 (35.5) | 1 | 19 |
| pBI-519HCC | 14 | 3 (21.4) | 4 | 7 | 4 (28.6) | 3 | 7 |
| Total | 60 | 19 (31.6) | 10 | 31 | 23 (36.7) | 7 | 30 |
| Control[b] PRSV-YK (18-2-4) | 5 | 0 | 0 | 5 | 5 | 0 | 0 |
| NT | 5 | 0 | 0 | 5 | 0 | 0 | 5 |

[a]15, 31 and 14 transgenic lines were derived from the three constructs, pBI-519HCF, pBI-519HCN and pBI-519HCC, wherein five plants of each line were mechanically inoculated with PRSV 5-19 or PRSV YK and the results were recorded 28 dpi (day post inoculation).
[b]PRSV YK-CP transgenic papaya lines 18-2-4 highly resistant to PRSV YK (Bau et al. 2003), but susceptible to PRSV 5-19 (Tripathi et al. 2004) and non-transgenic papaya (NT) were used as controls.
[c]Susceptible lines showed symptoms of mosaic on leaves after inoculation with PRSV 5-19 or YK 14 dpi. Resistant lines showed a one-two week delay in symptom development as compared to that of the controls. Highly resistant lines showed no symptoms at 28 dpi.
[d]All PRSV 5-19 resistant or highly resistant lines were also highly resistant to PRSV YK.

5. Indirect Enzyme-Linked Immunosorbent Assays (ELISA)

Indirect ELISA was performed as described previously (Yeh and Gonsalves, 1984). Obtained leaf extracts from PRSV inoculated transgenic papaya lines diluted (1:100) in 50 mM sodium carbonate buffer (pH 9.6) with 0.01% sodium azide were used for coating on wells of a 96-well microtiter plate for ELISA. The PRSV CP antiserum (Yeh et al. 1984), diluted 2000-fold in conjugate buffer (Yeh et al. 1984), was added (200 µl/well) and incubated at 37° C. for 1 hr. After washing the wells three times, alkaline phosphatase-conjugated goat anti-rabbit immunoglobulin (KPL, Inc., Gaithersburg, Md., USA), diluted 5000-fold in conjugate buffer, were added to each well. After washing, p-nitrophenyl phosphate (Sigma-Aldrich Corporation, St. Louis, Mo., USA) was added to each well. The absorbance at 405 nm was measured with a Rainbow microplate reader (SLT Lab Instruments, Salzburg, Austria). When plantlets of each lines were analyzed by ELISA with polyclonal PRSV CP antibody as described above, the results revealed that the absorbance of highly resistant transgenic plantlets was similar to that of mock-inoculated healthy controls and the absorbance of the plantlets with symptoms was recorded two-fold or more as compared to that of the nontransgenic lines inoculated with PRSV 5-19 or YK. The results indicated that the accumulation of the challenge viruses is completely inhibited in the highly resistant lines.

6. Analysis of Copy Numbers of the Transgene by Southern Blotting

Sixteen transgenic papaya lines with high resistance against PRSV 5-19 and PRSV YK, including 5 pBI-519HCF, 9 pBI-519HCN and 2 pBI-519HCC were selected and subject to analysis as follow for determining copy numbers of the transgene.

DNeasy Plant Mini kit (Qiagen, Valencia, Calif., USA) was used to extract genomic DNA of papaya plants. Genomic DNA was digested with AseI and separated by electrophoresis on a 0.8% agarose gel followed by removal of purine, unwinding helixes and neutralization with buffers. DNA on gel was transferred to Hybond-N+ membrane (Amersham Pharmacia Biotech, UK) and crossed linked under UV light for 5 mins. Twenty-five ng DNA fragment amplified from pBI-519HCF using primer pair 519HCStopA/519HCSacB was labeled as a HC-Pro specific probe by Primer-It II random primer labeling kit (Stratagene, LaJolla, Calif., USA) according to manufacturer's instruction. The blotted membrane was treated with hybridization of the probe at 60° C. overnight. After washing of the membrane, autoradiography of the treated membrane was carried out at −80° C. for 48 hr on an X-ray film (Hyperfilm MP, Amersham Phamacia Biotech, UK) with intensifying screens (Hyperscreen™, Amersham Phamacia Biotech, UK) for comparison of differences of copy numbers between resistant and susceptible lines.

Figure 3:
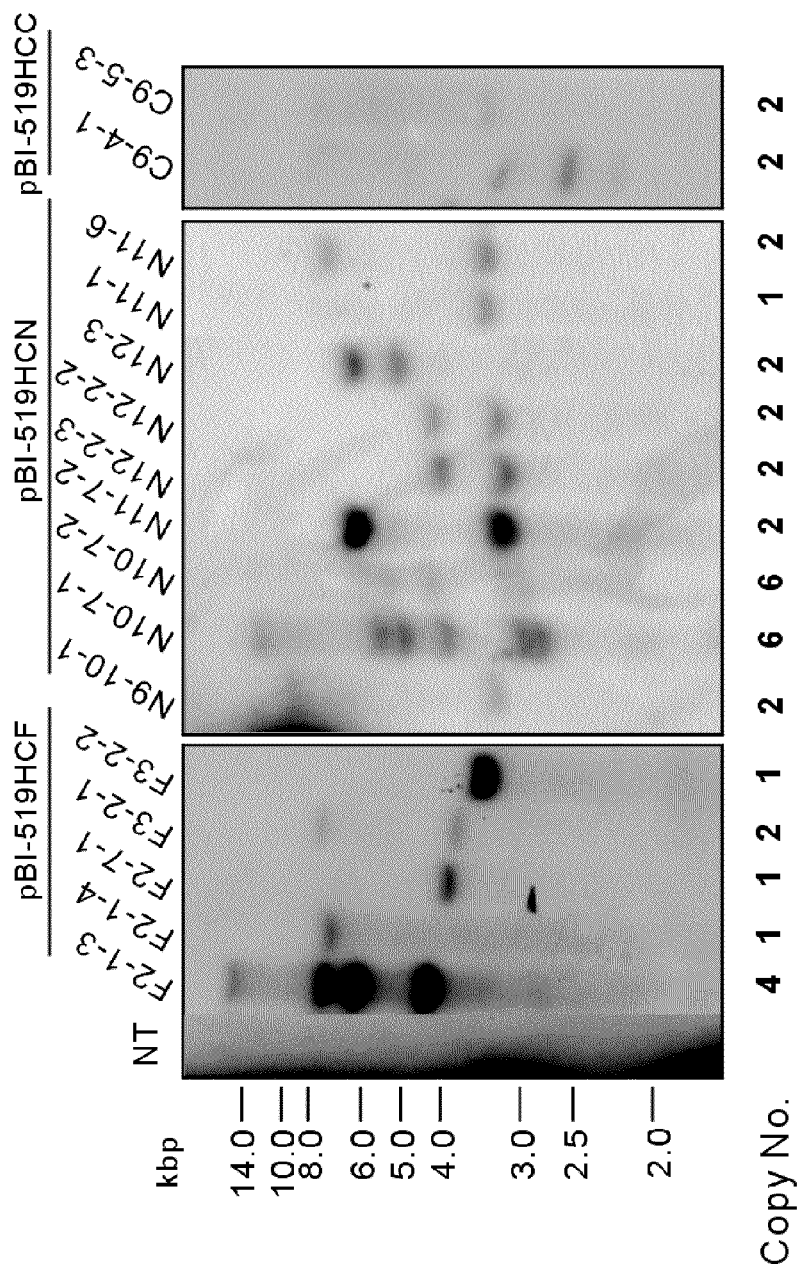
FIG. 3 illustrates insertion of transgene in the transgenic papaya lines analyzed by Southern blotting.

The copy number (copy No.) of the transgene was shown in FIG. 3 as indicated at the bottom of each lane, wherein non transgenic papaya lines were used as control; the four lines F2-1-4, F2-7-1, F3-2-2 and N11-1 had single copy of transgene insert; and other lines had two and more copies of transgene inserts.

7. Evaluation of Resistance Against Different Geographic PRSV Strains

The highly resistant lines were further inoculated with PRSV strains (5-19 and YK) and other different geographic PRSV strains including Mexico (MX), Thailand (TH) and Hawaii (HA) for selecting transgenic papaya lines with broad-spectrum resistance to different geographic PRSV strains.

The nucleotide and amino acid sequences of HC-Pro gene or CP gene of PRSV 5-19, and published PRSV strains TH, MX, YK and HA were compared in Table 2 and FIGS. 5A to 5D. The sequence of the HC-Pro gene of the line 5-19 shares nucleotide identities ranging from 86.1 to 96.8% with those of YK, MX, TH and HA. The sequence of the CP gene of 5-19 shared nucleotide identities ranging from 89.4 to 95.9% with those of YK, HA, TH, and MX. The lines F2-1-4, F2-7-1, F3-2-2, N11-1 and F3-2-2 with one insert of the transgene were further analyzed for their broad-spectrum resistance to different geographic PRSV strains and the lines NT and 18-2-4 were used as control.

The results of viral resistance analysis of the lines at fourteen, twenty-eight and forty two days after inoculation were shown in Table 3. Non-transgenic control (NT) showed symptoms 14 days after inoculation with various viruses. Line 18-2-4 showed high resistance to PRSV YK and delayed resistance to MX, TH and HA, but susceptible to PRSV 5-19. Lines F2-1-4 and N11-1 showed resistances to PRSV YK and 5-19 and had delayed resistance to TH and HA, but susceptible to MX. Line F3-2-2 showed complete resistance to all PRSV strains, indicating that HC-Pro gene could be a target gene for providing broad-spectrum resistance to other papaya ringspot virus that has at least 86.1% homology.

TABLE 2

Comparison of nucleotide and amino acid identities of HC-Pro (in upper corner) and CP (in lower corner) coding regions of PRSV isolates from Taiwan and other geographic areas

| | Identity (nucleotide/amino acid) | | | | |
|---|---|---|---|---|---|
| Virus strains[a] | 5-19 | YK | TH | HA | MX |
| 5-19 | ... | 96.8[b] | 91.1 | 86.8 | 86.1 |
| | ... | 98.7[c] | 96.5 | 95.8 | 95.0 |
| YK | 95.9 | ... | 91.0 | 86.5 | 85.8 |
| | 97.9 | ... | 96.1 | 95.6 | 95.0 |
| TH | 92.8 | 92.6 | ... | 86.1 | 91.8 |
| | 97.1 | 95.3 | ... | 95.2 | 96.1 |
| HA | 90.7 | 91.2 | 90.1 | ... | 84.7 |
| | 91.8 | 92.3 | 92.8 | ... | 94.3 |
| MX | 89.4 | 89.8 | 94.6 | 88.9 | ... |
| | 94.2 | 93.7 | 93.7 | 93.3 | ... |

[a]Sources for the HC-Pro and CP sequence of PRSV 5-19 was from You (2005) and Tripathi et al. (2004), PRSV YK from Wang and Yeh (1997), and PRSV HA was from Yeh (1992). The HC-Pro sequences of PRSV MX and TH were determined in this investigation. Sequence comparison was conducted with PC/GENE software (version 6.85, IntelliGenetics, Inc., Mountain View, CA).
[b]Nucleotide sequence identity.
[c]Amino acid sequence identity.

TABLE 3

Responses of $R_0$ plants of selected transgenic lines carrying untranslatable full-length (F lines) or partial (N line) silencing suppressor HC-Pro gene after mechanical inoculation with five strains of Papaya ringspot virus originating from different geographic regions

| | | Number[a] of plants with symptoms after inoculation | | | | |
|---|---|---|---|---|---|---|
| Lines | Dpi | 5-19 | YK | MX | TH | HA |
| NT | | | | | | |
| | 14 | 5 | 5 | 5 | 5 | 5 |
| | 28 | 5 | 5 | 5 | 5 | 5 |
| 18-2-4 | | | | | | |
| | 14 | 5 | 0 | 0 | 0 | 0 |
| | 28 | 5 | 0 | 3 | 2 | 3 |
| | 42 | 5 | 0 | 5 | 3 | 4 |
| F2-1-4 | | | | | | |
| | 14 | 0 | 0 | 4 | 0 | 0 |
| | 28 | 0 | 0 | 5 | 1 | 1 |
| | 42 | 0 | 0 | 5 | 4 | 4 |
| F2-7-1 | | | | | | |
| | 14 | 0 | 0 | 5 | 5 | 2 |
| | 28 | 0 | 0 | 5 | 5 | 3 |
| | 42 | 0 | 0 | 5 | 5 | 4 |
| N11-1 | | | | | | |
| | 14 | 0 | 0 | 5 | 0 | 0 |
| | 28 | 0 | 0 | 5 | 2 | 3 |
| | 42 | 0 | 0 | 5 | 5 | 5 |
| F3-2-2 | | | | | | |
| | 14 | 0 | 0 | 0 | 0 | 0 |
| | 28 | 0 | 0 | 0 | 0 | 0 |
| | 42 | 0 | 0 | 0 | 0 | 0 |

[a]Numbers indicate plants showing symptoms as determined from five plants of each of the lines F2-1-4, F2-1-7, N11-1 and F3-2-2.
NT = non-transgenic control. Strains from Taiwan = YK, Hawaii = HA, Thailand = TH, and Mexico = MX. Responses of the inoculated plants were recorded at 14, 28, 42, 42 days after inoculation and PRSV PK coat protein transgenic papaya line 18-2-4 (Bau et al., 2003) was used as control.

8. Transgene Transcript (mRNA) and siRNA Detection by Northern Blotting

Twelve transgenic papaya lines derived from constructs as described above were selected. The transgenic papaya from each construct included three lines with high resistance to virus and one line susceptible to virus and transgene transcript and siRNA thereof were detected as follow.

Total RNA was extracted from young leaves of transgenic and non-transgenic papaya plants by the ULTRASPECTM RNA isolation system (Biotecx Laboratories, Houston, Tex., USA). Fifteen μg of total RNA for each sample was separated on a 1.2% agarose gel containing formaldehyde, transferred to Hybond-N+ membrane (Amersham Pharmacia Biotech, UK) and hybridized with a $\alpha$-$^{32}$P labeled probe specific to the HC-Pro coding regions of PRSV 5-19, prepared with Primer It II random primer labeling kit (Stratagene), at 60° C. for 16 hr. Prehybridization, hybridization, washing, and autoradiography were carried out as described for Southern hybridization analysis. After washing, autoradiography of the membrane was carried out at −80° C. for 48 hr on an X-ray film (Hyperfilm MP) with intensifying screens (Hyperscreen™). According to the results of the Northern blotting and comparison of amounts of transcripts between the highly resistant lines and susceptible lines, the underlying mechanism of viral resistance was confirmed to be dependent from post-transcriptional gene silencing (PTGS).

For the detection of the siRNA derived from the transgenic constructs, thirty micrograms total RNA as described above was resolved by 15% polyacrylamide gel elctrophoresis [15% polyacrylamide, 1×TBE (8.9 mM Tris, 8.9 mM boric acid, 20 mM EDTA, 8 M urea gel], transblotted to a Hybond-N+ membrane (Amersham Phamacia Biotech, UK) and subject to cross-linking under UV light for 5 mins Hybridization was carried out using the ULTRAHyb-Oligo solution (Ambion Inc., Austin, Tex.) according to manufacturer's directions at 42° C. for 1 hour prehybridization and the $\alpha$-$P^{32}$ labeled 5-19 HC-Pro probe specific to the coding sequence as described above was added and incubated at 42° C. for 16 hours. After washing, autoradiography of the washed membrane was carried out at −80° C. for 48 hr on an X-ray film with intensifying screens. Differences among transgenic lines susceptible to PRSV viruses were compared. The Dynamarker® Prestain Marker (BioDynamics Laboratory Inc., Tokyo, JAPAN) for small RNA was used as markers in this experiment.

Figure 4:
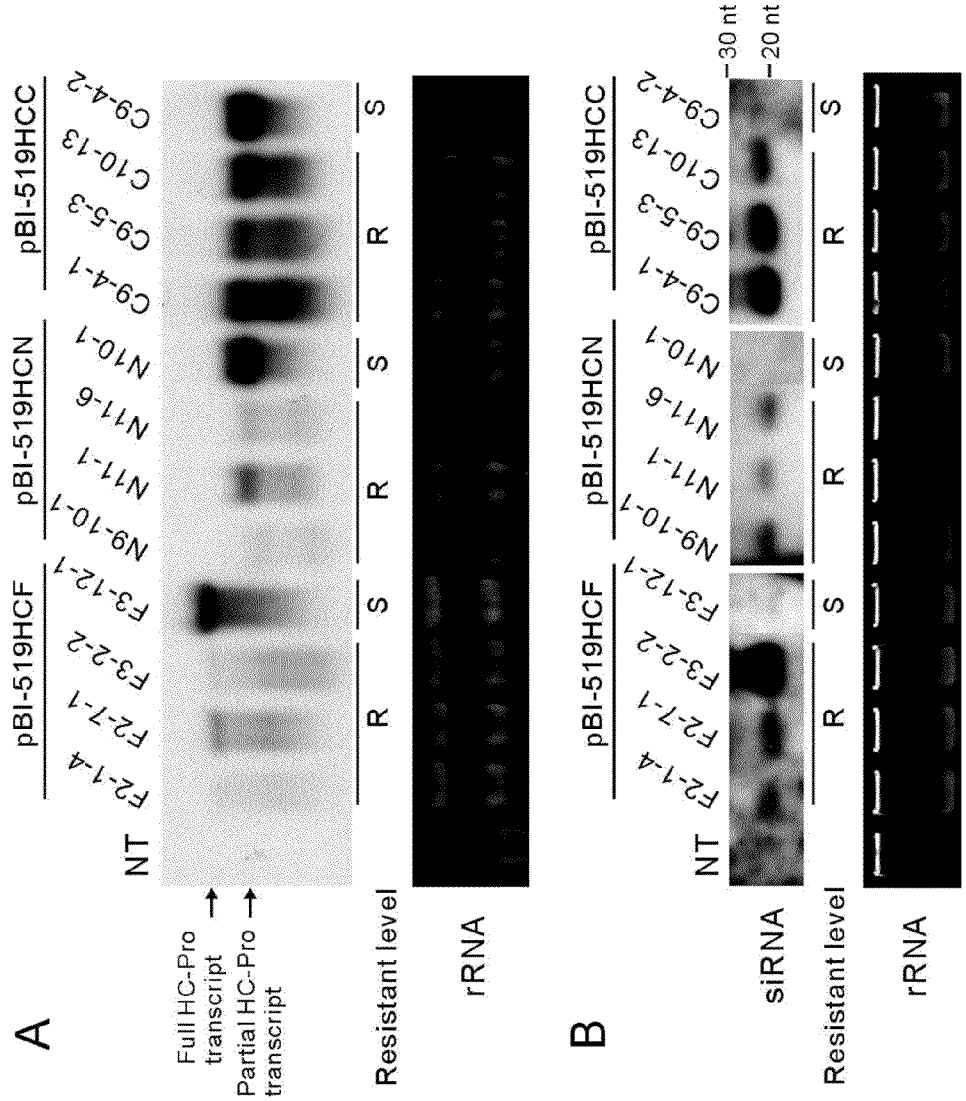
FIG. 4 illustrates expression of the transgene transcript and siRNA detected by Northern blotting.

The expression levels of transgene transcripts were shown in FIG. 4A, wherein transcripts were not detected in the lines with high levels of resistance against virus. A smear of transcripts was observed in each of the lines C9-4-1, C9-5-3 and C10-13, indicating that higher levels of the transgenic transcripts were accumulated and suggesting that mRNA had been degraded. The accumulation of siRNA was observed as shown in FIG. 4B, wherein siRNA was detected from the resistant (R) lines but not from the susceptible (S) lines, indicating that the untranslatable constructs of HC-Pro are useful in providing plants with resistance against virus through PTGS mechanism.

9. Analysis of Inheritance of HC-Pro Transgene and Resistance to $R_1$ Progeny Two resistant lines, F2-1-4 and F3-2-2, with one copy of transgene were self-crossed to obtain R1 progeny. The premature zygotic seeds obtained 90 days after self-crossing of each R1 progeny were collected and cultured in MSNB medium containing 100 mg/l kanamycin for determining the inheritance of the nptII gene. The premature embryos that possessed the nptII gene developed calli vigorously and grew as plantlets, while those without the nptII gene did not develop calli, remained pale and eventually perished. The aforementioned plantlets were transferred to a greenhouse and analyzed for their resistance against PRSV 5-19.

Results showed that 88 of 117 premature zygotic seeds of the lines F2-1-4 were resistant to kanamycin and 77 of 102 premature zygotic seeds of the line F3-2-2 were resistant to kanamycin. Seventy-seven kanamycin-resistant papaya plantlets of F3-2-2 were transferred to a greenhouse and inoculated with PRSV 5-19, and the results revealed high levels of resistance. This indicated that the untranslatable constructs of HC-Pro are useful in providing plants with resistance against virus by PTGS and the resistance is capable of being inherited by their progenies.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A recombinant plasmid that confers resistance against Papaya ringspot virus to a plant or plant part, comprising a binary vector containing a control sequence and a coding sequence fragment of Papaya ringspot virus helper-component protease gene (PRSV HC-Pro), wherein the coding sequence fragment is operably linked to the control sequence and said coding sequence is selected from the group consisting of SEQ ID NOs: 5, 6, and 7, or is a nucleotide sequence of at least 85% homologous with SEQ ID Nos: 5, 6, or 7, having at least one stop codon at the 5' end of the nucleotide sequence.

2. A recombinant plasmid, comprising a binary vector containing
a coding sequence fragment having at least 85% homology with the sequence set forth in SEQ ID NO: 5 and having at least one stop codon at the 5' end of said coding sequence, operably linked to a control sequence.

3. A recombinant plasmid, comprising a binary vector containing
a coding sequence fragment having at least 85% homology with the sequence set forth in SEQ ID NO: 6 and having at least one stop codon at the 5' end of said coding sequence, operably linked to a control sequence.

4. A recombinant plasmid, comprising a binary vector containing
a coding sequence fragment having at least 85% homology with the sequence set forth in SEQ ID NO: 6 and having at least one stop codon at the 5' end of said coding sequence, operably linked to a control sequence.

5. The recombinant plasmid of claim 1, wherein the coding sequence fragment is located downstream of the control sequence.

6. The recombinant plasmid of claim 2, wherein the coding sequence fragment is SEQ ID NO: 5 and wherein the recombinant plasmid is from the *E. coli* transformant deposited in the China Center for Type Culture Collection under CCTCC accession number CCTCC M 2010112.

7. The recombinant plasmid of claim 1, wherein the coding sequence fragment is a nucleotide sequence selected from the group consisting of SEQ ID NOs: 6 and 7.

8. A recombinant microorganism prepared by transforming a microorganism with the recombinant plasmid of claim 1.

9. The recombinant microorganism of claim 8, wherein the microorganism is disarmed *Agrobacterium tumefaciens*.

10. A method for providing plant with resistance against Papaya ringspot virus, comprising steps of:
introducing the recombinant plasmid of claim 1 into a plant or plant part, wherein:
(i) the transcripts of the coding sequence fragment of the Papaya ringspot virus helper-component protease gene are not translationally expressed, and
(ii) helper-component proteases are not expressed,
whereby the plant or plant part has resistance against Papaya ringspot virus.

11. The method of claim 10, wherein the plant is selected from the group consisting of: plants belonging to Cucurbitaceae and Caricaceae.

12. The method of claim 10, wherein the step of introducing the recombinant plasmid of claim 1 into a plant or plant part includes:
introducing the recombinant plasmid into a *Agrobacterium* sp. to obtain a recombinant *Agrobacterium* sp.; and
infecting the plant or plant part with the recombinant *Agrobacterium* sp. to obtain a plant having the coding sequence fragment.

13. A method for generating a plant with resistance against Papaya ringspot virus, comprising: providing (A) a nucleotide sequence selected from the group consisting of SEQ ID Nos: 5, 6 and 7, or (B) a nucleotide sequence at least 85% homologous with SEQ ID Nos: 5, 6 or 7, having at least one stop codon at the 5' end of the nucleotide sequence, wherein the nucleotide sequence is operably linked to a control sequence; and introducing the nucleotide sequence into a plant or plant part to obtain a plant with resistance against Papaya ringspot virus.

14. The method of claim 13, wherein the nucleotide sequence is a fragment of the sequence set forth in SEQ ID NO: 8.

15. A recombinant plant cell that has resistance against Papaya ringspot virus, comprising a genome containing (A) a sequence selected from the group consisting of: SEQ ID Nos: 5, 6 and 7, or (B) a nucleotide sequence at least 85% homologous with SEQ ID Nos: 5, 6 or 7, having at least one stop codon at the 5" end of the nucleotide sequence, wherein the nucleotide sequence is operably linked to a control sequence.

* * * * *